(12) United States Patent
Anker et al.

(10) Patent No.: US 9,179,865 B2
(45) Date of Patent: Nov. 10, 2015

(54) LUMINESCENT TENSION-INDICATING ORTHOPEDIC STRAIN GAUGES FOR NON-INVASIVE MEASUREMENTS THROUGH TISSUE

(71) Applicant: Clemson University, Clemson, SC (US)

(72) Inventors: Jeffrey Anker, Greenville, SC (US); Melissa Rogalski, Central, SC (US); Dakota Anderson, Orangeburg, SC (US); Jonathon Heath, Florence, SC (US)

(73) Assignee: Clemson University, Clemson, SC (US)

( * ) Notice: Subject to any disclaimer, the term of this patent is extended or adjusted under 35 U.S.C. 154(b) by 142 days.

(21) Appl. No.: 13/960,881

(22) Filed: Aug. 7, 2013

(65) Prior Publication Data

US 2014/0046191 A1    Feb. 13, 2014

Related U.S. Application Data

(60) Provisional application No. 61/680,419, filed on Aug. 7, 2012.

(51) Int. Cl.

| | | |
|---|---|---|
| *G01L 1/24* | (2006.01) | |
| *A61B 5/11* | (2006.01) | |
| *A61B 5/00* | (2006.01) | |
| *A61B 6/00* | (2006.01) | |
| *A61B 17/68* | (2006.01) | |
| *G01L 1/25* | (2006.01) | |
| *A61B 17/86* | (2006.01) | |

(52) U.S. Cl.
CPC .............. *A61B 5/1127* (2013.01); *A61B 5/0075* (2013.01); *A61B 5/0077* (2013.01); *A61B 5/0084* (2013.01); *A61B 5/45* (2013.01); *A61B 5/4504* (2013.01); *A61B 5/686* (2013.01); *A61B 5/6867* (2013.01); *A61B 6/00* (2013.01); *A61B 17/68* (2013.01); *G01L 1/25* (2013.01); *A61B 17/86* (2013.01); *A61B 2562/0261* (2013.01)

(58) Field of Classification Search
CPC ........ G01L 1/25; G01L 1/241; A61B 5/0084; A61B 5/0075; G01N 2203/0647
USPC ..................... 73/760, 800, 862.624
See application file for complete search history.

(56) References Cited

U.S. PATENT DOCUMENTS

| | | | |
|---|---|---|---|
| 3,987,699 | A | 10/1976 | Popenoe |
| 4,793,751 | A | 12/1988 | Takeuchi et al. |
| 4,904,132 | A | 2/1990 | Popennoe |
| 7,730,846 | B2 | 6/2010 | Pett et al. |
| 8,280,484 | B2 | 10/2012 | Boyden et al. |

(Continued)

OTHER PUBLICATIONS

Agayan, R. R.; Horvath, T.; McNaughton, B. H.; Anker, J. N.; Kopelman, R. *Proc. SPIE 2004*, 5514, 502.

(Continued)

*Primary Examiner* — Max Noori
(74) *Attorney, Agent, or Firm* — Dority & Manning, P.A.

(57) ABSTRACT

Strain gauges that can provide information with regard to the state of implantable devices are described. The strain gauges can exhibit luminescence that is detectable through living tissue, and the detectable luminescent emission can vary according to the strain applied to the gauge. A change in residual strain of the device can signify a loss of mechanical integrity and/or loosening of the implant, and this can be non-invasively detected either by simple visual detection of the luminescent emission or through examination of the emission with a detector such as a spectrometer or a camera.

27 Claims, 6 Drawing Sheets

(56) References Cited

U.S. PATENT DOCUMENTS

| | | | |
|---|---|---|---|
| 2005/0171434 A1 | 8/2005 | Madden et al. | |
| 2006/0058627 A1* | 3/2006 | Flaherty et al. | 600/409 |
| 2007/0239054 A1* | 10/2007 | Giftakis et al. | 600/513 |
| 2009/0156912 A1* | 6/2009 | Kuhn et al. | 600/310 |
| 2011/0264009 A1* | 10/2011 | Walter et al. | 600/595 |

OTHER PUBLICATIONS

Allison, S.; Heyman, J., Nondestructive ultrasonic measurement of bolt preloaded using the pulsed-phase lockedloop interferometer. *Welding, Bonding and Fastening*, 1984 p. 197-209(SEE N 86-11227 02-23) 1985.

* cited by examiner

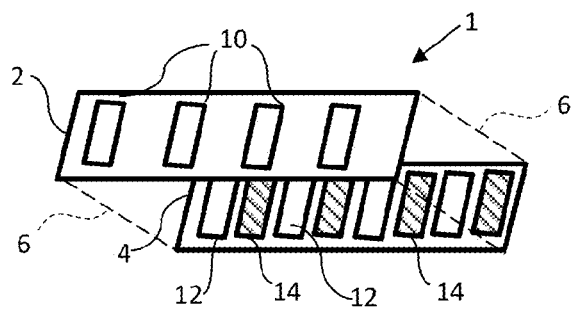
FIG. 1
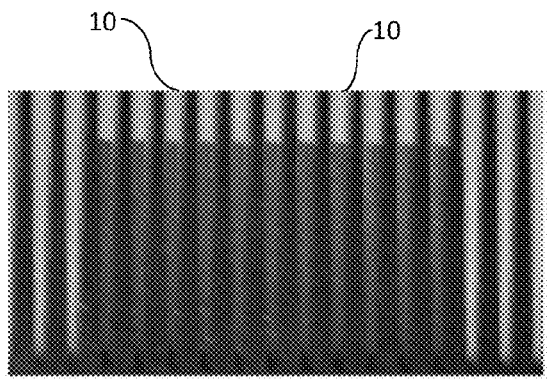
FIG. 2A
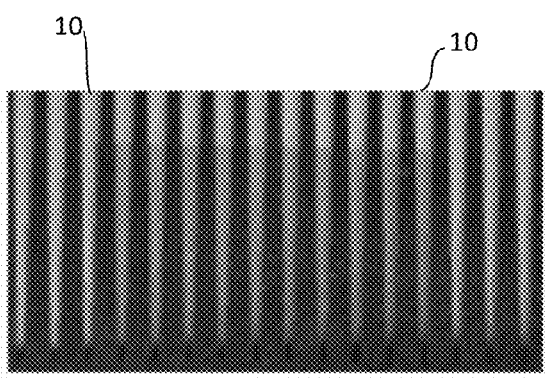
FIG. 2B
FIG. 2
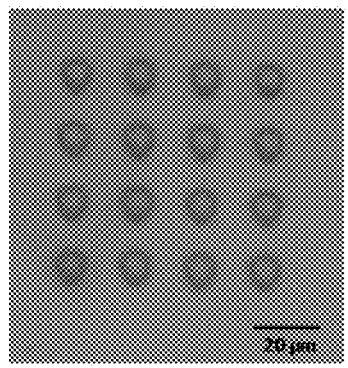
FIG. 3

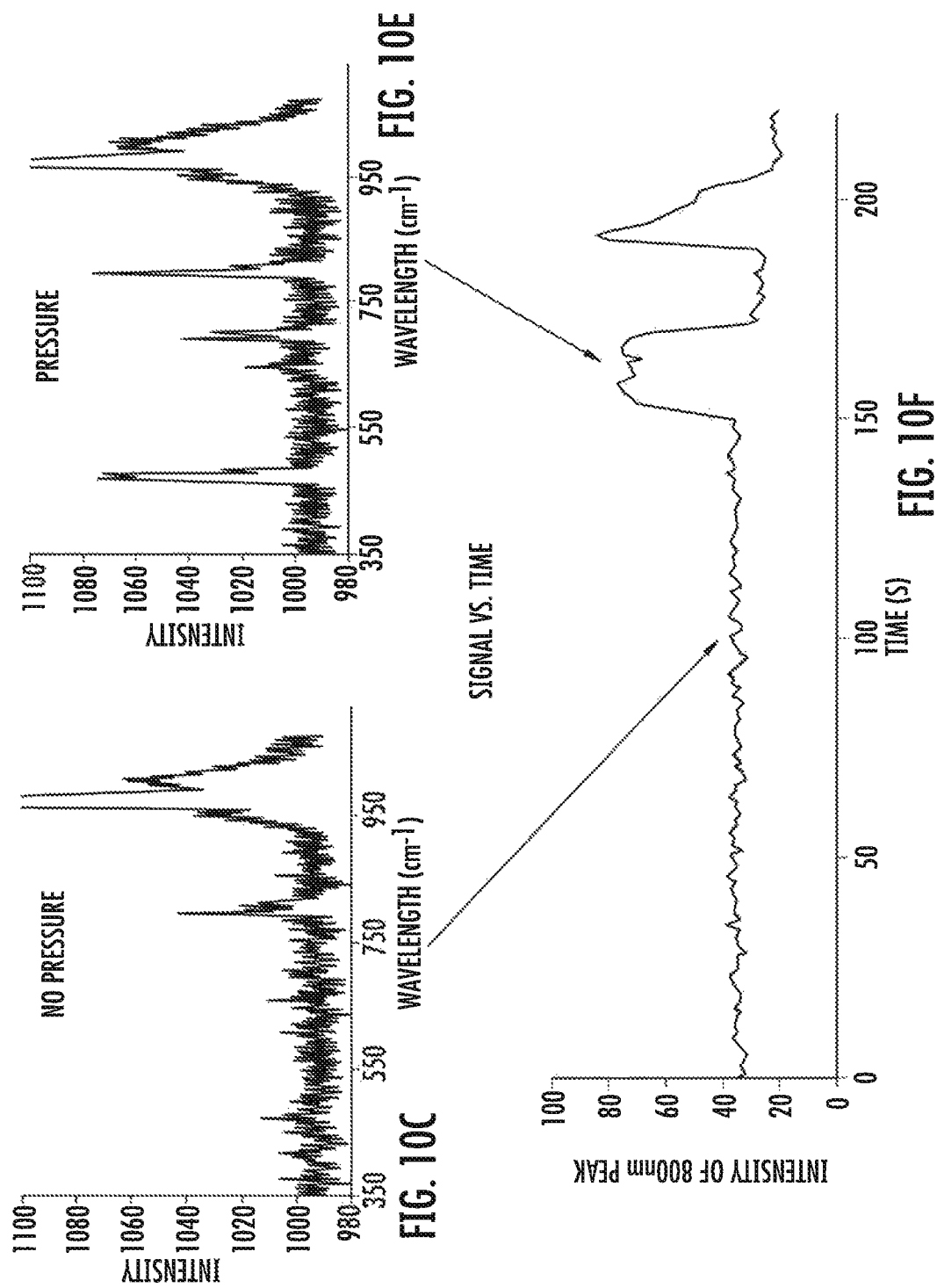

LUMINESCENT TENSION-INDICATING ORTHOPEDIC STRAIN GAUGES FOR NON-INVASIVE MEASUREMENTS THROUGH TISSUE

CROSS REFERENCE TO RELATED APPLICATION

This application claims filing benefit of U.S. Provisional Patent Application Ser. No. 61/680,419 having a filing date of Aug. 7, 2013, which is incorporated herein by reference.

STATEMENT REGARDING FEDERALLY SPONSORED RESEARCH OR DEVELOPMENT

This invention was made with government support under grant no. NNX10AM76H awarded by NASA and under grant nos. RR021949 and GM103444 awarded by the NIH. The government has certain rights in the invention.

BACKGROUND

Over 28 million musculoskeletal injuries are treated annually in the US, including approximately 2 million fracture fixation surgeries. While fixation is highly effective, refracture, malunion and non-union can occur, especially if load bearing begins before proper healing. Other potential problems include loosening from infection (5-10% of cases) and aseptic loosening. All of these problems relate to the mechanics of the implant and bone, and methods to detect the in situ stress are important in determining proper treatment course.

There are two known classes of fixation devices: external fixation devices, where pins pass through the skin and are locked with an external plate, and internal devices, with all materials implanted. External devices can be easily instrumented with electronic strain sensors and bone stiffness can be measured by applying known stresses to the pins and measuring the resulting strain. These external measurements are a highly promising diagnostic for bone healing. The rate of stiffening has been used to diagnose non-union, and using specific stiffness endpoints can reduce the average time until load bearing by weeks while also reducing the number of refractures due to premature load bearing in unhealed fractures. However, external fixation devices are more prone to infection than internal fixation devices and are less often used. For internal fixation devices, currently available strain sensors (e.g. resistive and capacitive strain gauges, fiber optic Bragg gratings, ultrasound of liquid-filled cavities, X-ray diffraction, optical moiré pattern analysis, and video tracking) are either unsuitable for non-invasive transdermal measurements or require relatively large and complex devices for power, detection, and telemetry.

In addition to fracture fixation, mechanical measurements are also important in many other biomedical applications, including tendon repair. For example, the ability to make direct assessments of the mechanical capabilities of a tendon may help to prevent failures in various types of tendon repairs, such as rotator cuff repairs.

There are various known methodologies for measuring strain and displacement in the absence of tissue, such as various optical-based methods. Specifically, Moiré pattern analysis and photoelastic polarimetry are used to map strain fields, while video tracking is used to track the position of individual mechanical components. For example video tracking was used to measure the position of dots drawn on a tendon during stress in a cadaveric model in order to determine strain on the implant. The position and velocity of motors and stages are also often measured using the reflection from optically patterned rotational and linear optical encoders. In addition, strain indicating bolts are known that include a component that changes color based upon displacement of fluid during bolt elongation and relative displacement of two components. However, it has been found that the above optical techniques are insufficient for measuring implanted medical devices through tissue for three principle reasons. First, when using any of such optical techniques, most of the incident ambient light reflects directly from the skin and superficial tissue providing a large background that obscures the very dim signal from light which penetrates through the tissue, reflects from the optical strain gauge, and penetrates back through the tissue and skin. Second, even if there is no background, optical scattering of the reflected light in the tissue results in blurring of the image, with a point spread function approximately equal to the depth through the tissue. Third, the point spread function depends significantly upon the sample orientation and depth. Thus strain measurements that depend on optical imaging will not work through tissue.

Electrical impedance and optical fiber strain gauges have also been developed for studying dynamic strain in vivo, but these require transdermal wires which can easily lead to infection. In addition, wireless devices have been developed, but these require complex electronics for power, sensing, and telemetry, which limits the size and necessitates significant modification of the implants. Non-invasive methods usually rely upon tracking the position of fiduciary markers using X-ray or ultrasound imaging, but these are ineffective at measuring displacements less than about 100 micrometers ($\mu$m). X-ray images also require acquisition at multiple angles to account for changes in sample position and angle.

What are needed in the art are strain gauges that allow for displacement and/or strain on musculoskeletal structures and/or implantable devices to be measured optically through living tissue without the need for invasive technologies so as to limit patient stress and infection opportunities.

SUMMARY

According to one embodiment, disclosed is an implantable strain gauge. More specifically, the implantable strain gauge can include a first plate and a second plate that are held at a distance from one another and that are configured to be implanted within tissue. The second plate of the strain gauge includes a window. The second plate is movable relative to the first plate from a first position to a second position. In addition, the strain gauge includes a luminescent material. For instance the luminescent material can be on an upper surface of the first plate. An emission of the luminescent material is detectable through tissue. At the first position, the emission of the first luminescent material is detectable through the window. At the second position there is either no luminescent emission detected through the window or a second emission is detected through the window that differs from the emission that is detected through the window at the first position.

Implantable devices comprising the strain gauges are also disclosed. Devices can include, for example, fixation devices such as bolts, screws, pins, etc. as well as less rigid implants such as implantable gels.

Also disclosed is a method for detecting loads on an implant. The method includes detecting through living tissue two or more emissions from a strain gauge that is a component of the implant and determining a variation in strain being placed on the implant according to the variation between the first and second emissions.

BRIEF DESCRIPTION OF THE FIGURES

FIG. 1 schematically illustrates one embodiment of an implantable strain gauge as disclosed herein.

FIG. 2 illustrates top views of a strain gauge in a first position (FIG. 2A) and in a second position (FIG. 2B) with different luminescent spectra visible at each position.

FIG. 3 illustrates one pattern of luminescent material as may be incorporated in a strain gauge.

FIG. 10B illustrates a strain gauge under no tension and FIG. 10C presents the luminescent intensity spectrum of the gauge of FIG. 10B.

FIG. 10D illustrates the strain gauge of FIG. 10B under tension and FIG. 10E presents the luminescent intensity spectrum of the gauge of FIG. 10D.

FIG. 10F presents the intensity spectrum versus time for the strain gauge of FIGS. 10B-10E as tension is applied to the gauge.

DETAILED DESCRIPTION

Figure 4:
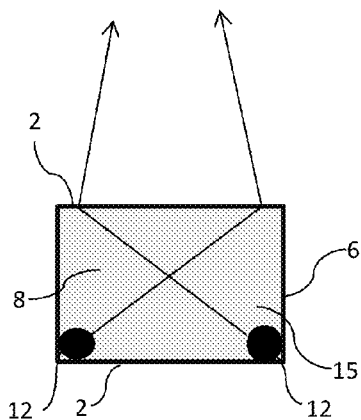
FIG. 4 schematically illustrates another embodiment of an implantable strain gauge as disclosed herein.

Reference now will be made in detail to various embodiments of the disclosed subject matter, one or more examples of which are set forth below. Each example is provided by way of explanation, not limitation. In fact, it will be apparent to those skilled in the art that modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

In general, the present disclosure is directed to strain gauges that can provide information with regard to the state of implantable devices. More specifically, the strain gauges can exhibit luminescence that is detectable through living tissue, and the detectable luminescent emission can vary according to the strain applied to the gauge. A change in strain of the device can signify a loss of mechanical integrity and/or loosening of the implant, while increases in stiffness and load sharing can indicate normal bone healing processes. These strain measurements can be non-invasively detected either by simple visual detection of the luminescent emission or through examination of the emission with a detector such as a spectrometer or a camera.

The strain gauge can be sensitive, robust, and show minimal sensitivity to changes in observation distance and angle. The strain gauge can also provide desired information both rapidly and remote to the implant site of the gauge so as to provide a route to verify strain in structural components of implantable devices. In one embodiment, high resolution strain gauges can be formed that can provide information with regard to minute changes, for instance during structural loading.

In one embodiment, the strain gauge can be a moiré-type strain gauge that includes a pattern of one or more luminescent materials on a plate and a window over the plate through which an element of the luminescent pattern can be detected. The plate and window can be located on or in an implantable device such that displacement of the window with respect to the plate when the gauge is under tension causes the luminescent pattern that is detected through the window to change. In another embodiment, the strain gauge can include a luminescent material that will exhibit a variation in emission (e.g., intensity variation, emission wavelength variation, etc.) under pressure variation. For instance, the strain gauge can include a luminescent material in conjunction with an elastomer and when the gauge is under tension the elastomer can apply pressure to the luminescent material causing a variation in the luminescent emission that is visible through the window layer of the gauge.

It should be appreciated that, as used herein, the term "window" generally refers to any opening(s), material(s), surface feature(s) and/or the like that provides for the transmission of a luminescent emission therethrough. For instance, as will be described below, windows may be formed via openings defined in an upper plate of the disclosed strain gauge, with such openings remaining un-filled or being filled-in with a transparent or semi-transparent material(s). Alternatively, windows may be defined in the upper plate by forming all or portions of the plate with a transparent or semi-transparent material(s). For example, in a specific embodiment, the entire upper plate may be formed from a transparent material(s), with one or more coatings being applied to the upper plate to form windows therein.

Beneficially, the gauge can be formed with high sensitivity such that it is sensitive to very small displacements, for instance displacements a fraction of a width of a pattern element in moiré-type gauge, with sensitive limitations primarily being due to limits on printing uniformity and/or luminescent material/window alignment. The disclosed strain gauges do not depend upon the angle or precise placement of the strain gauge in order to obtain useful information. Miniature gauges can be readily fabricated and applied to surfaces of implantable devices.

Referring to FIG. 1, one embodiment of a strain gauge 1 is illustrated. The strain gauge 1 includes an upper plate 2 and a lower plate 4 held at a distance from one another. The substrate material that forms the upper plate 2 and the lower plate 4 can be the same or different from one another. For instance, in one embodiment, the lower plate 4 can be rigid, while the upper plate 2 can exhibit an amount of flexibility. In any case, both the upper plate 2 and the lower plate 4 can be formed of biocompatible, implantable materials including polymers, metals, ceramic, or composite materials including a combination of implantable materials. By way of example, and with no limitation, the upper plate 2 and lower plate 4 can include implantable polymers such as polyetheretherketone (PEEK), polyetherketone (PEK), polyaryletherketone (PAEK), polyethylene, polycarbonates, polyurethanes, and so forth. A polymeric material can include a polymer in conjunction with additives as are known in the art, such as reinforcement fibers formed of glass, ceramic, polymers, etc.

The upper plate 2 can include one or more windows 10. The windows 10 can be openings formed in the upper plate 2, with no material covering the windows 10, or can be formed of a solid transparent or semi-transparent material, such as a glass or transparent polymer (e.g., polyacrylic). Alternatively, the upper plate 2 may be formed from a transparent material(s), with one or more coatings being applied to the transparent plate to form the windows 10. In such an embodiment, the coating(s) applied to the upper plate 2 need not be just transparent or opaque. For instance, one or more different colored coatings may be applied to the upper plate 2 to create semi-transparent windows.

The windows 10 of the upper plate 2 can be formed according to any suitable process. For instance, in one embodiment, a solid plate can first be formed and then material can be removed from the plate in select areas to create the windows in the plate. In those embodiments in which the windows are formed of a transparent material, a multi-layered plate can be formed that includes a first layer of a transparent material and an adjacent layer of an opaque material. The opaque material can then be removed in selected areas to leave the transparent windows in the plate.

Any removal process can be utilized in forming the windows 10. By way of example, plasma etching, dry etching, chemical etching, laser etching and the like can be utilized.

The lower plate 4 is patterned with areas 14 that include a luminescent material. For instance, the luminescent material can lie between the upper plate 2 and the lower plate 4. In one embodiment, second areas 12 can also include a luminescent material for which the luminescent emission differs from that of the luminescent material of the first areas 14. In another embodiment, the second areas 12 do not include a luminescent material, but in either case, the areas 14, 12 can be differentiated from one another by the differences in luminescent characteristics of the areas.

The luminescent material(s) included in the strain gauge can be any luminescent material for which the emission can be detected through tissue. For instance, the emission can be detected through about 10 centimeters or less of tissue, about 8 centimeters or less of tissue, or about 5 centimeters or less of tissue. In one embodiment, the emission of the luminescent material can be detected through about 0.3 centimeters to about 10 centimeters of tissue, or about 1 centimeter to about 5 centimeters of tissue.

In general, the luminescent material can be excited to emission and can emit at a wavelength that can be detected through tissue. For instance, the luminescent material can emit at visible to near infrared wavelengths (e.g., from about 390 nanometer to about 1500 nanometers) and in one embodiment at red to near infrared wavelengths (e.g., from about 600 nanometers to about 1500 nanometers) so as to be detectable through tissue either visually or by use of a suitable detector such as a camera or a spectrometer. The luminescent emission of the materials can be excited by any suitable irradiation. In one embodiment, the luminescent emission can be excited by near-infrared, infrared, or X-ray irradiation, providing an essentially background-free signal able to penetrate through several centimeters of tissue. In one embodiment, the luminescent material can utilize infrared/near infrared excitation as well as infrared/near infrared emission, this can provide a strain gauge that presents minimal photodamage as well as minimal background autofluorescence interference from surrounding biomolecules.

The luminescent material can include fluorescent or phosphorescent dyes. Near infrared fluorophores can include, without limitation, IRdye800CW™ (available from LiCOR) and CY7 (available from Amersham), as well as near infrared lanthanide chelates. Other red and near infrared emitting fluorophores as may be utilized include cyanine dyes such as Cy5, Cy5.5, and Cy7 (Amersham Biosciences, Piscataway, N.J., USA) or a variety of Alexa Fluor dyes such as Alexa Fluor 633, Alexa Fluor 635, Alexa Fluor 647, Alexa Fluor 660, Alexa Fluor 680, Alexa Fluor 700, and Alexa Fluor 750 (Molecular Probes-Invitrogen, Carlsbad, Calif., USA), and the like. Other fluorophores as may be utilized include those described in U.S. Pat. No. 8,372,868 to Bornhop, et al., U.S. Pat. No. 8,280,484 to Boyden, et al., and U.S. Patent Application Pub. No. 2005/0171434 to Madden, et al., all of which are incorporated herein by reference.

Red and near infrared phosphorescent dyes can be utilized including, without limitation, phosphorescent transition-metal complexes including Cu(I), Cu(II), Cr(III), Re(I), Re(III), Ru(II), Os(II), Ir(III), Pt(II), Pd(II), Au(I), and Au(III) complexes such as metallated quinones, phosphorescent metalloporphyrins, and the like. Some suitable porphyrin complexes include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes include, but not limited to, platinum(II) tetra-mesofluorophenylporphine, platinum(II) octaethylporphine ketone (PtOEPK), and palladium(II) tetra-meso-fluorophenylporphine. Bipyridine metal complexes may also be utilized, examples of which include, but are not limited to, bis[(4,4'-carbomethoxy)-2,2'-bipyridine] 2-[3-(4-methyl-2, 2'-bipyridine-4-yl)propyl]-1,3-dioxolane ruthenium (II); bis (2,2'-bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2,2'-bipyridine)ruthenium (II); (2,2'-bipyridine) [bis-bis(1,2-diphenylphosphino)ethylene] 2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butan-e]ruthenium (II); bis(2,2'-bipyridine)maleimidohexanoic acid, 4-methyl-2,2'-bipyridine-4'-butylamide ruthenium (II), and so forth.

In one embodiment, the luminescent materials can be provided in the form of particles. For example, upconversion or surface enhanced Raman spectroscopy (SERS) micro- or nanoparticles can be utilized as a luminescent material that can, in one embodiment, utilize near infrared upconversion or radioluminescence. Upconversion particles can absorb near infrared (NIR) excitation light (e.g. from a 980 nm diode laser) and emit shorter wavelength fluorescence in the visible through near infrared spectrum. Because the particles absorb near infrared photons sequentially, the multiphoton cross-section is orders of magnitude smaller than tissue, and excitation intensities of $mW/cm^2$ can be sufficient for intense excited upconversion with essentially no tissue autofluorescence. For applications requiring continuous acquisition over long periods, for instance to study dynamics of a system, it may be preferred to utilize upconversion particles, as they do not require ionizing radiation.

Upconversion particles can include, without limitation, rare-earth doped inorganic particles, especially those doped with Yb and excited with 980 nm light, or Er, and excited by 1523 nm, such as but not limited to $NaYF_4$:Yb/L, $NaLuF_4$:Yb/L, $NaYF_4$:Er, $Gd_2O_2S$:Yb/L, $Y_2BaZnO_5$,Yb/L, $Y_2O_3$:Yb/L, $LuPO_4$:Yb/L, $YbPO_4$:L. $BaCl_2$:Dy/Er $NaGdF_4$:Yb/L, where L is a dopant such as Eu, Er, Tb, Ce, Pr, Nd, Dy, Ho, Sm, Tm, Tb, Mn. The particles may also be excited by sequential absorption 1523 nm light in Er doped materials as well as absorption of light from excited states using two or more different wavelengths of light. The particles may have internal cores including iron oxide cores, and external shells such as $CaF_2$ and organic components.

Radioluminescent particles that generate visible luminescence upon X-ray irradiation can be utilized as a luminescent material. X-ray irradiation can provide higher resolution imaging to, e.g., resolve multiple strain gauges at different locations on an implant. For example, 300 μm resolution, limited by the X-ray beam width, can be utilized to map strain fields by measuring strain at multiple locations, each with its own luminescent strain sensor, or measure the luminescent pattern after passing through a moire patterned surface or photoelastic material between cross-polarizers attached to the implant surface. X-ray excited materials can include, without limitation, NaI, CsI, $SrI_2$, $CaWO_4$, lanthanide halide scintillators doped with a rare earth dopant such as Ce, Tb, or Eu, $Gd_2O_3$, Eu:CdTe quantum dots, anthracene nanoparticles, and Tb labeled actin. In one embodiment, europium and cesium doped $LaF_3$ and $LuF_3$ nanoparticles can be utilized as these materials have a high quantum efficiency and reasonable stability. In another embodiment, $Gd_2O_2S$:Eu nanoparticles can be used that are also highly luminescent and can be fabricated with a wide range of sizes and shapes including core-shell particles with multiple functionalities to the cores and shells (e.g. an upconversion core, a spacer layer, and a radioluminescent shell). $Gd_2O_2S$:Tm particles can be utilized in one embodiment. These particles are non-cytotoxic up to 1 mg/mL, are well characterized as MRI contrast agents, and have intense upconversion and radioluminescence signals. Rare earth based oxide/oxysulfide particles can be utilized in one embodiment as they are quite photostable, have long lifetime, and easily distinguished narrow spectral peaks.

In general, a microparticle can have an average diameter of less than about 900 micrometers (μm), less than about 500 μm, or less than about 100 μm. A nanoparticle generally includes a particle having an average diameter of about 500 nanometers (nm) or less, about 100 nm or less, about 50 nm or less, or about 20 nm or less. Luminescent nanoparticles can exhibit high quantum efficiency, stability, and a relatively long lifetime to allow efficient energy transfer. In one embodiment, the particle can have a diameter of from about 5 nm to about 10 μm.

Particles can generally be of any shape. For instance, particles can be generally circular, ovoid, amorphous, or spindle shaped. The shape of a particle can generally depend upon materials of formation and/or formation conditions.

The luminescent material can generally exhibit an emission lifetime on the order of microseconds (μs), e.g., about 15 μs or less, such as from about 1 to about 10 μs.

Referring again to FIG. 1, a moire-type strain gauge can include a luminescent material in one or more areas 14 on a surface of the lower plate 4. In one embodiment, the strain gauge can include first areas 14 that include a first luminescent material 14 and second areas 12 that include a second luminescent material. The emission of the two areas 12, 14 will differ from one another.

The plates 2, 4 can be arranged so that only one area 14 or 12 can be viewed through the window at a time. For instance, the area 14 that includes the luminescent material can have a linewidth substantially equal to the width of the window 10 such that at most one emission spectrum is visible through the window that is located above the area. For example, when the device of FIG. 1 is under little or no strain, each area 12 can be aligned with a window 10. Upon displacement of the upper plate 2 with respect to the lower plate 4 each area 14 will become visible through the windows 10. This will alter the visible luminescence emission, for instance due to a loss or gain of an emission, through a variation in emission wavelength, emission lifetime, or the like.

FIG. 2 illustrates one embodiment in which the strain gauge is at rest at FIG. 2A and under tension at FIG. 2B. As can be seen, at FIG. 2A a first, darker color is visible through the windows 10, while at FIG. 2B, the upper plate has moved and a lighter color is visible through the windows 10.

The pattern of luminescent material can be formed according to any suitable process. For example, areas of luminescent material can be fabricated on a substrate by inkjet printer, which can form pattern elements of about 1 mm or less, about 800 μm or less, or about 600 μm or less in width and any suitable length.

To increase sensitivity, for instance to quantify minute changes in strain during structural loading and vibration, the line width of a patterned area 14 can be small. For instance, the line width of a pattern element can be reduced by use of high resolution inkjet photo printers, which can form a pattern element about 60 micrometers or less in width (e.g. 9600× 2400 dpi corresponds to 52 μm for lines that are 20 dots wide and arbitrarily long). For further reduction, photolithography or micro-ink printing using a bioforce enabler can be utilized, which can form a pattern element to a width of less than about 30 micrometers in width, for instance from about 1 micrometers to about 20 micrometers in width. Photolithography, imprint lithography, and electron beam lithography may be used to make even smaller features. The approach can be scaled up using printing press techniques, such as reel-to-reel flexo-printing. Fine features may also be formed by recursive sequential deposition of layers onto a substrate (e.g. printing a 10 μm black layer, followed by a clear layer, followed by a black layer etc., or sequential deposition using electrochemical approaches), with this substrate then being sectioned vertically.

While the luminescent materials can be located on a surface of a strain gauge in a linear pattern, this is not a requirement of the devices, and the luminescent materials can be applied in any suitable fashion. By way of example, FIG. 3 illustrates an example of micropatterned luminescent materials formed with a bioforce enabler on a glass substrate. This technique allows sub-micrometer precision in depositing droplets containing a luminescent material (e.g., upconversion particles) over large areas using an AFM-like technique.

In principle, the sensitivity of a moire-type strain gauge is limited by the width of the pattern elements of the luminescent materials. For a given line width, sensitivity is ultimately limited by shot noise in the intensity of the color channels in the detector which limits acquisition speed. Preliminary results demonstrate a noise level of ~0.1% dynamic range. This may be improved by more accurately spaced lines and color pallet. In one embodiment, systematic errors due to changes in lighting, camera distance, camera angle, and hysteresis can be held to a level less than or comparable to 1% of the dynamic range. While not wishing to be bound to any particular theory, it is believed that distance and angle effects can be minimal, provided that the area of luminescent material can be clearly resolved. Light conditions (e.g. indoors vs. outdoors in external structural applications, or spectral distortion from tissue scattering in internal applications) may cause significant interference and nearby calibration standards may be needed to adjust for light conditions. For example, reference standards may be used to account for tissue scattering based upon one or several points. A one point calibration corresponds to a region with a known spectrum that is illuminated through the tissue to measure the effect of tissue absorption and scattering on the luminescence spectrum. This single reference could be located at a specific region of the implant or could be excited by an alternate mechanism than the patterned substrate in the strain gauge (e.g. X-ray luminescence when the patterned strain gauge excites with 980 nm light, or an Er-doped upconversion reference that excites with 1523 nm light, or an upconversion phosphor that excites by sequential absorption of photons from two different near infrared wavelengths). A preferred embodiment for a two point calibration would be two regions, one with a luminescence spectrum corresponding to the strain gauge at one end of its dynamic range, and a second region with a luminescence spectrum corresponding to a pattern at the other end of its dynamic range. These reference regions could be formed by fixing (e.g. gluing) a mask to a patterned substrate positioned so that only one luminescent feature could be seen through either gauge. A third standard region would be a "dark region" coated with a thin layer of an opaque material such as a black carbon pigment or a reflective material such as aluminum.

There can be a trade-off between sensitivity and dynamic range of the strain gauge. Smaller lines provide greater displacement sensitivity but have a smaller dynamic range. This conundrum can be resolved using two or more distinct luminescent materials for different areas of the gauge or spectral peaks that measure strain on different scales, similar to a vernier scale (e.g. red/blue measures displacements from 2-100 µm, green/black measures displacement from 50-500 µm).

Referring again to FIG. 1, the upper plate 2 and lower plate 4 can be connected to each other, for instance by use of pliable walls, posts, or the like such that the upper and lower plates can move with respect to one another. For instance, as shown in FIG. 1, sidewalls 6 (shown in dashed lines) may be utilized to couple the upper plate 2 to the lower plate 4. In one embodiment, the upper and lower plates can be connected to one another with a solid wall, such that the interior portion of the strain gauge 1 that contains the luminescent material is enclosed. This may be desired in one embodiment to isolate the luminescent materials from the surrounding environment, but it is not a required feature of the device. In another embodiment, the upper plate 2 and lower plate 4 can be independently attached to a medical device, for instance within a bore formed in the device, with the upper and lower plates 2, 4 in proper alignment with one another and the upper plate 2 visible at or near a surface of the implantable device. In this embodiment, the upper and lower plates are not directly attached to one another, but rather are each separately attached to an implantable device.

FIG. 4 illustrates another embodiment of the strain gauge. According to this embodiment, the upper plate 2 and the lower plate 4 can be at a distance from one another and connected to one another with a wall 6, posts, or the like such that the strain gauge defines a space 8 between the upper plate 2 and the lower plate 4. Within the space 8, the gauge can include an elastomer 15.

In one embodiment, the elastomer can be a thermoplastic elastomer such as a siloxane polymer. Some examples of suitable siloxane elastomers include, without limitation, polydimethyl siloxanes such as dimethylvinylsiloxy end group-capped polydimethyl siloxane, methyldivinylsiloxy end group-capped polydimethyl siloxane, dimethylvinylsiloxy end group-capped dimethyl siloxane, (80 mol %)/methylphenylsiloxane (20 mol %) copolymers, dimethylvinylsiloxy end group-capped dimethylsiloxane (80 mol %)/diphenylsiloxane (20 mol %) copolymers, dimethylvinylsiloxy end group-capped dimethylsiloxane (90 mol %)/diphenylsiloxane (10 mol %) copolymers, and trimethylsiloxy end group-capped dimethylsiloxane/methylvinylsiloxane copolymers. Besides the above-mentioned polymers, other polymers may also be utilized. For instance, some suitable vinyl-modified silicones include, but are not limited to, vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; polydimethylsiloxane, mono vinyl, mono n-butyldimethyl terminated; and vinylphenylmethyl terminated polydimethylsiloxanes. Further, some methyl-modified silicones that can be used include, but are not limited to, dimethylhydro terminated polydimethylsiloxanes; methylhydro, dimethylpolysiloxane copolymers; methylhydro terminated methyloctyl siloxane copolymers; and methylhydro, phenylmethyl siloxane copolymers.

In conjunction with the elastomer 15, the gauge can include a luminescent material that can exhibit a difference in emission depending upon the pressure of the material's surrounding environment. For instance, the gauge can include luminescent particles 12 that can be, e.g., upconversion particles and/or surface enhanced Raman spectroscopy nanoparticles embedded in the elastomer 15. In one embodiment, the particles can be functionalized, for instance by use of silane chemistry, and encapsulated in a thin silica film prior to being incorporated in the elastomeric polymer. This can prevent any unwanted interactions with bodily fluids and effectively eliminate any potential cytotoxicity of the luminescent material. During use, changes in strain to the gauge can displace the upper plate 2 relative to the lower plate 4 and cause an increase in pressure in the elastomer 15. This increased pressure can, in turn, lead to spectral changes in the detectable emission of the luminescent particles 12 embedded in the elastomer 15.

In one embodiment, the gauge can further include a luminescent dye between the luminescent particles 12 and the upper plate 2. In this embodiment, pressure applied to the device can increase or decrease the amount of dye visible through the window of the upper plate 2, which can further alter the characteristics of the emission that is visible through the window of the upper plate 2.

According to this embodiment, upconversion luminescence from the particles 12 can pass through the elastomer 15 between the particles 12 and the window in the upper plate 2 as illustrated by the directional arrows in FIG. 4. The thickness of the elastomer 15 between the particles 12 and window can increase or decrease under tension. The elastomer can be dyed with luminescent dye, for instance a near infrared absorbing dye, providing a tension/path length-dependent emission spectrum. According to Beer's law, the transmittance through an absorptive film is given by: $T=10^{-\epsilon bc}$. For example, when considering the fluorophore Cy7 $\epsilon_{(780\ nm)}$=of $1.5 \times 10^5$ $M^{-1}cm^{-1}$, and $\epsilon_{(800\ nm)}$=$4 \times 10^4$. Thus, a 1 mM layer 100 µm thick will transmit only 3% of 780 nm light, but 40% of 800 nm light, while a 1 µm path length will transmit at 97% and 99% respectively. The log of the peak ratio is expected to be proportional to tension. The slope of the log depends upon the wavelengths selected, which provides a large dynamic range. A calibration curve can be obtained by measuring the luminescence spectrum under different loads applied by a universal testing machine. Calibrations can be performed at different tissue depths and polynomial fitting can be carried out to account for nonlinearities due to the specific fluorescence of the dye, absorption of scattered light by the elastomer, and the finite width of the band pass.

Figure 5:
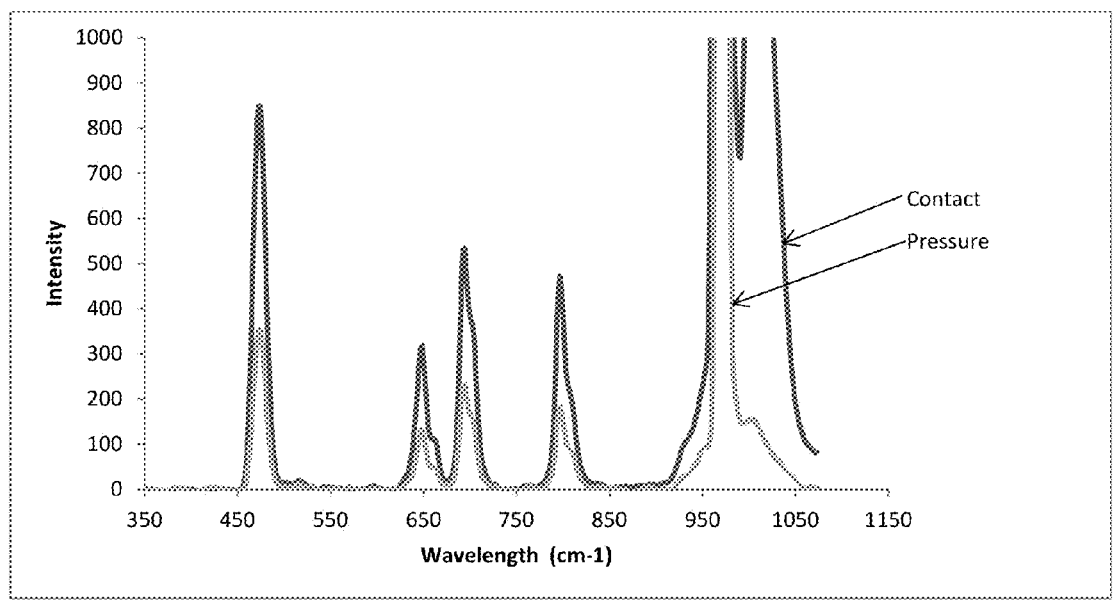
FIG. 5 illustrates the intensity of luminescence for a strain gauge as illustrated in FIG. 4 under low and increased pressure.

FIG. 5 illustrates the emission intensity of a strain gauge as illustrated in FIG. 4 under tension (pressure) and under no tension (contact). As can be seen, the emission intensity varies greatly depending upon the strain condition of the gauge, and thus the strain of the system can be determined relatively simply through examination of the emission spectrum of the gauge.

During use, tissue scattering, absorption and thickness can affect the upconversion and radioluminescence spectrum of the luminescent materials and thus strain accuracy. Based upon photon migration models and preliminary results, it is believed that the intensity of radioluminescence can decrease by an order of magnitude with increasing tissue depth and there will be a red-shift in luminescence of collected light that can be overcome by either using closely space spectral reference peaks or lifetime-based detection. In any case, there can be sufficient signal for measurements up to several centimeters deep.

Beneficially, a strain gauge can be easily sized to be accommodated into or onto any desired implantable device. For instance, the base of a gauge can be of any suitable shape including square, rectangular, triangular, etc. with a maximum cross sectional dimension of about 1 $cm^2$ or less. A gauge can generally have a relatively small height, with a distance between the upper plate 2 and the lower plate 4 of about 1 mm or less, for instance about 400 μm or less. Thus, a strain gauge can be located within or on an implantable device with the upper plate 2 either flush or below the surface of the device, though the upper plate of the device should be available for detection of the luminescent emission from the window(s) of the device.

In addition, the strain gauges can be sterilizable, e.g., autoclavable, so as to be incorporated in an implantable device and sterilized prior to implantation. They can also be sealed in a sterile container prior to use.

The strain gauges can be utilized in conjunction with any implantable structural devices such as, without limitation, fixation devices such as bolts, screws, pins, balloon catheters, stents, etc. In another embodiment, the implantable device can be a less rigid device. For example, the strain gauge can be associated with an implantable gel that can interact with the surrounding tissues and provide information with regard to localized pressure. For instance, a strain gauge can be incorporated with an implantable gel that can swell or contract in response to an analyte. Upon interaction with the analyte, the tension of the gel can change due to the swelling/contraction, and the strain gauge can exhibit a variation in the luminescent spectrum that can then be detected as described herein. Analytes that can be detected by use of such an embodiment can include both physical and chemical analytes including, without limitation, glucose, proteins (e.g., enzymes such as proteases), temperature, pH, electrostatic interactions, etc.

Figure 6:
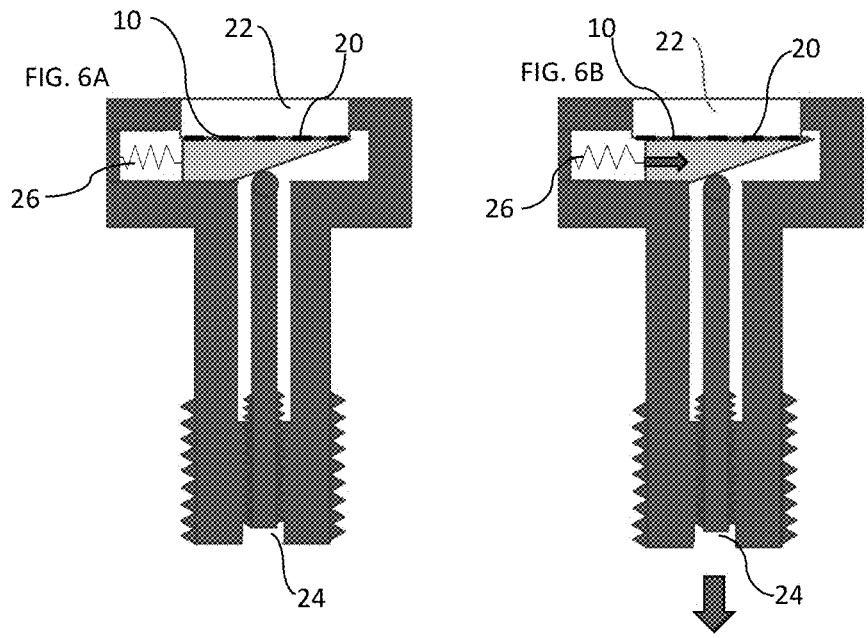
FIG. 6 schematically illustrates one embodiment of an implantable tension indicating bolt as may incorporate the strain gauge of FIG. 1.

FIG. 6 is a schematic for a tension indicating bolt that can incorporate a moiré-type strain gauge 20 as described herein. An opening 22 in the bolt head can allow one to observe the emission from the strain gauge 20 that is pressed against the opening 22 by a central pin 24 below and a spring 26 on the left. When the bolt is under tension, the central pin 24 can extend away from the window 22 as shown by the lower directional arrow in FIG. 6, allowing the spring 26 to urge the strain gauge to the right. Displacement of the gauge is observed as an emission change as a different pattern line becomes visible through the window 10 due to the reference pattern of luminescent material in the strain gauge 20. In one embodiment, the bolt and/or the strain gauge can include structures so as to maintain proper alignment of the gauge within the bolt. For instance, the gauge and or bolt can include a dovetail, a trench and matching extension, or the like such that the gauge 20 and the surrounding bolt are aligned and proper alignment is maintained during operation.

Figure 7:
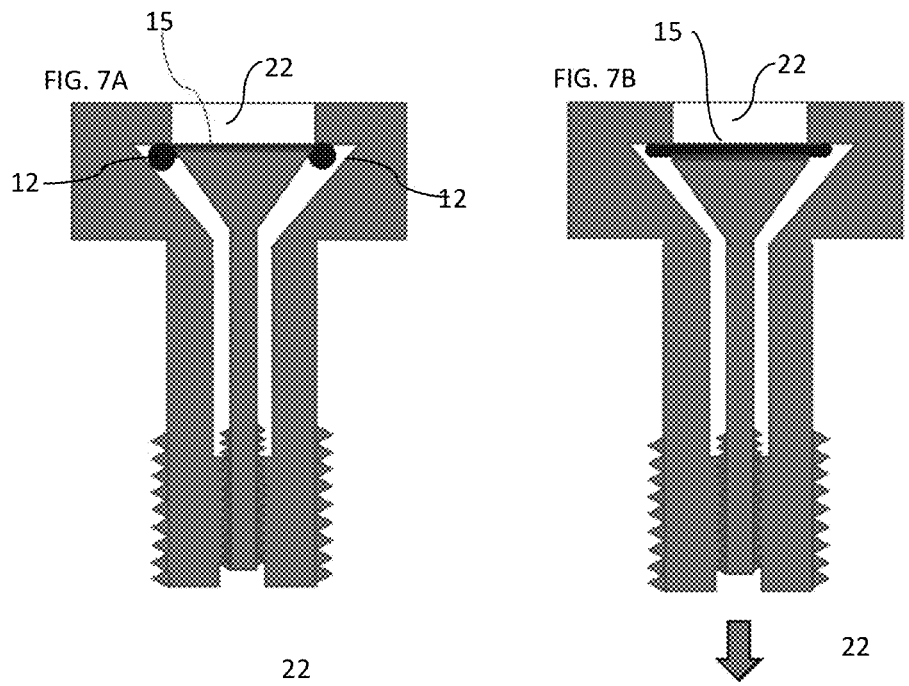
FIG. 7 schematically illustrates one embodiment of an implantable tension indicating bolt as may incorporate the strain gauge of FIG. 4.

FIG. 7 schematically illustrates a tension indicating bolt that can incorporate a strain gauge as illustrated in FIG. 4. According to this embodiment, when the bolt is under tension, it elongates and causes the central pin 24 to extend away from the opening 22 and alter the tension on the gauge. Displacement of the gauge is observed as an emission change as the pressure on the elastomer 15 in the gauge varies, which causes a variation in the emission spectra from the luminescent particles 12, the variation being visible through the opening 22.

When considering an implantable device such as a bolt, at proper bolt tension, the bolt strain is proportional to stress: $\epsilon=\sigma/E$, where c is the bolt strain ($\Delta L/L_0$), σ is the stress, and E is the young's modulus. For carbon steel, the young's modulus E ~200 GPa, and 90% of the yield stress is ~500 MPa. Therefore, the strain at 90% of yield stress corresponds to 25 μm elongation per centimeter of bolt length, or 64 μm elongation for a 1 inch long bolt. In FIG. 6, the pressure of the central pin 24 against the gauge forces the gauge left causing a change in emission visible through the window 10. Elongation of the bolt by 64 μm releases the strain gauge to the right by 64*/m, where m is the slope of the member's inclined plane. For a slope of 2, a 90% strain corresponds to a lateral displacement of about 130 μm. Thus, in one embodiment, the strain gauge can exhibit a variation in detected luminescence in this 130 μm range.

It should be appreciated that the disclosed strain gauges may be used to measure residual strain when an implant is unloaded, or may measure the stiffness when strains are applied. To measure the stiffness of a loaded/strained implant, any suitable force application means may be used to apply a force against the implant in vivo. For example, in one embodiment, loads may be applied indirectly to the implant, such as by having a patient bare weight on a scale. Alternatively, loads may be applied directly to the implant, such as by using magnets or any other suitable load application device. For example, magnetic field gradients may be used to apply a force to magnetic components on the implant, or oriented magnetic fields may be used to apply torques. It has been found that the use of magnetic forces to apply loads to implants has several advantages, namely that the magnetic forces may be applied non-invasively through tissue, may be easily modulated to modulate the strain and improve signal to noise ratio, and may be used in extendable/contractable orthopedic devices. Alternatively, loads may be applied to the implant using any other suitable means, such as by using thermally triggered materials (e.g., shape memory materials).

The present invention may be better understood with reference to the Examples described below.

Example 1

Figure 8:
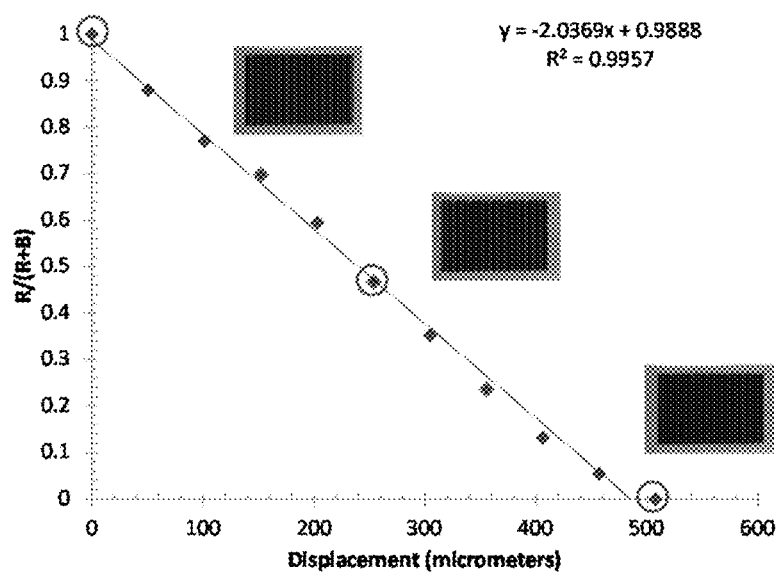
FIG. 8 graphically illustrates the response of a strain gauge to stress.

A strain gauge as illustrated in FIG. 2 was formed. The gauge included a series of lines that were printed with a color laser printer on a piece of paper and detected with a Nikon D90 digital camera. The lower plate was the paper that included the series of lines. A transparent film was utilized as a window layer. The lines were 500 μm thick, providing a dynamic range of 500 μm; a root mean square displacement resolution of 10 μm was obtained (root mean square displacements of less, for instance about 0.5 μm can be obtained in other embodiments). The transparency was made to slide smoothly above the patterned paper by folding the sides of paper around the edges of the transparency to make a rail (in place of the folded paper rail, more recent version have used laminating pouches). FIG. 8 shows results of the strain gauge used to measure displacement in a bone fracture mimic. The strain can be applied to a wide variety of other structural components.

The ratio between normalized red and total (blue+red) intensities varied linearly with strain. The line was a least squares linear fit to the points; a noise level of +/−10 μm rms was observed, corresponding to 670 μstrains for the 1.5 cm long strain gauge. The insets are photos of the strain gauge at the three circled points.

Another strain gauge with 500 μm lines was then attached to a 316 stainless steel dog bone-shaped specimen. The specimen was stretched in an Instron mechanical testing machine under a force ramp. Displacement was measured with the instron's linear variable differential transformer (LVDT) sensor and by measuring the color of the optical strain gauge with a Nikon D90 digital camera. The short term noise on the digital camera was ~0.5 μm, corresponding to 0.1% of the line width, and the shape of the displacement curve with the optical gauge agreed well with the LVDT.

Example 2

Figure 9:
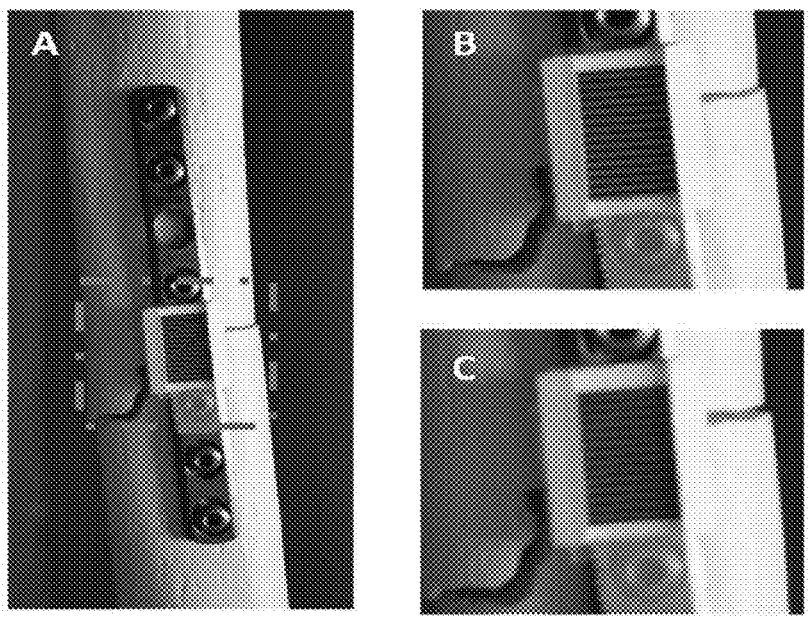
FIG. 9 illustrates a strain gauge measuring the strain between two surfaces including images of the gauge under low stress (FIG. 9A and FIG. 9B) and under high stress (FIG. 9C).

A mimic of a femur bone fracture was formed and an optical moiré phase-type strain gauge was attached to the fracture fixator as illustrated in FIG. 9A. The visible color of the gauge varied when it underwent strain. The visible pattern of the optical strain gauge measuring the strain between the two surfaces changed color from red (FIG. 9A and FIG. 9B) under no strain to blue (FIG. 9C) upon application of stress.

Example 3

A strain gauge including a film of upconversion luminescent material $Gd_2O_2S$:Yb/Eu microparticles (Phosphor Technologies Inc. product number PTIR475/F) embedded in a layer of polydimethylsiloxane was formed and including a crystal violet dye held in the gauge in conjunction with the luminescent material and the polydimethyl siloxane.

Figure 10A:
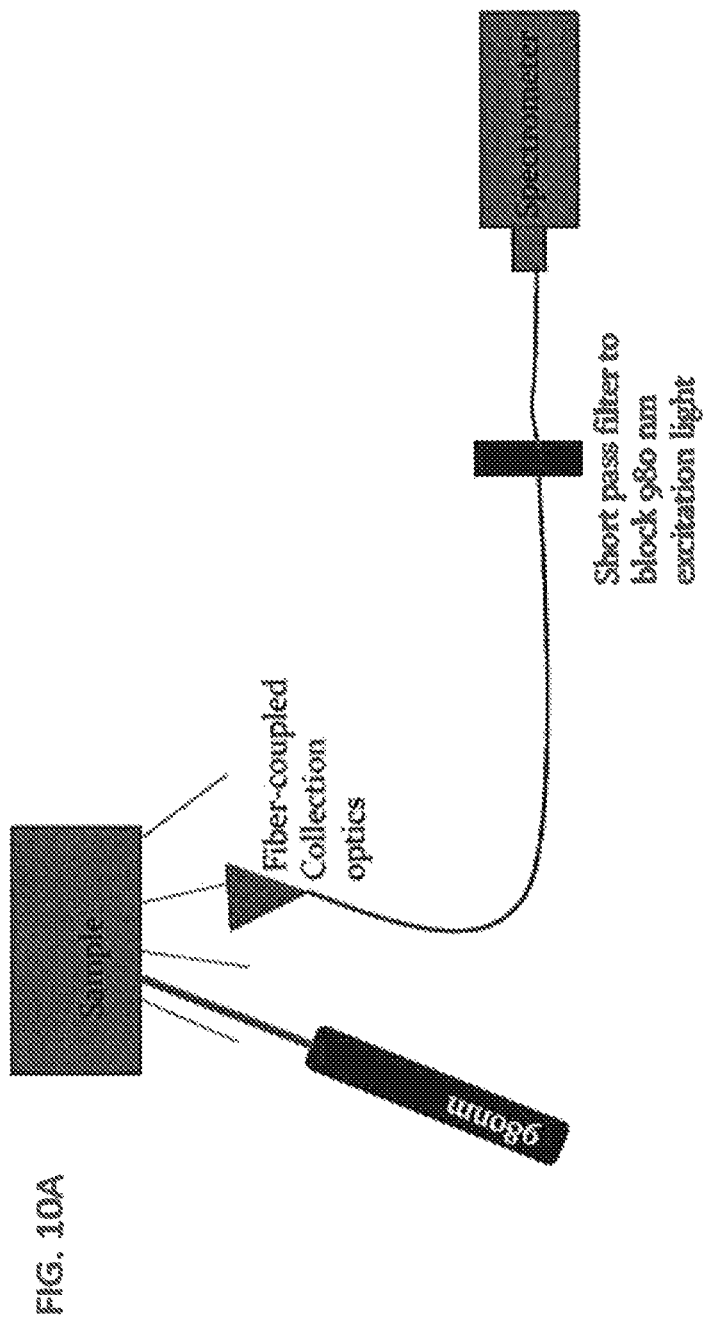
FIG. 10A illustrates one embodiment of a detection method for utilization in conjunction with a strain gauge.

FIG. 10A illustrates the experimental setup including the sample and a 980 nm diode laser used to excite the luminescent material of the sample. The emission was collected via fiber-coupled collection optics and sent through a short pass filter to block out the excitation signal prior to the emission spectrum being detected by use of a spectrometer.

Figure 10D:
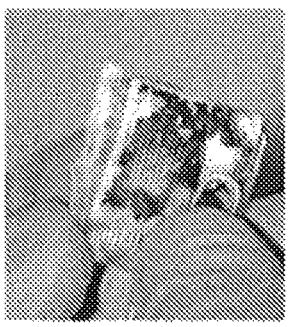
Figure 10B:

FIG. 10B is an image of the strain gauge without pressure applied, and FIG. 10C illustrates the spectrum from the gauge without pressure. As can be seen the emission spectrum shows only spectral peaks at greater than 750 nm. FIG. 10D illustrates the strain gauge after application of pressure, which displaced the dye held in the gauge. The spectrum of the gauge during the application of pressure (FIG. 10E) shows multiple spectral peaks below 750 nm. FIG. 10F illustrates the intensity of the 800 nm peak in time, acquired every 2 seconds, as pressure was rapidly applied at 150 seconds and again at 190 seconds.

Example 4

To show that the approach can apply to low modulus materials such as tendons as well as high modulus materials such as bones and steel, force was applied to a rubber section using a spring strain gauge, and the induced strain was measured by two methods: (a) looking at the color of a reflective strain gauge fixed to the rubber at two spots using clamps, and (b) using a ruler to measure the position of the two clamps. Stress and strain were calculated from load and displacement taking into account the length and cross-section of the rubber specimen. The two methods gave similar stress/strain curves.

Example 5

To show that magnets can be used to apply an external force to the disclosed strain gauges, iron staples were added to a piece of rubber associated with an optical strain gauge so that moving a magnet near the stapled end applied a force to the rubber. The resulting displacement was detected on the optical strain gauge.

Those skilled in the art will appreciate that such application of a magnetic force may achieved in variety of different ways including using magnetic materials with high coercivity (e.g., permanent magnets including but not limited to Alnico, NdFeB, or SmCo) or soft magnetic materials (e.g., including Fe, Ni, Co and allows thereof). Moreover, in addition to forces, torques may also be applied. For example, a 800 kA/m external magnetic field oriented 90 degrees to a 0.1 $cm^3$ NdFeB magnet with magnetization of 1 T would generate an in situ torques of ~0.08 Nm. Thus, if the magnet is attached to an extension screw with 40 threads per inch ($10^{-4}$ m/radian), such toque generates 80 N of axial force, assuming negligible friction. Of course, greater forces are possible using larger magnets and/or hydraulic systems or differential screws to increase the mechanical advantage.

It should also be appreciated that one may estimate the force from the magnetic properties of the material as well as the external magnetic field, but several assumptions may be needed for the calculations (for example, the field gradient depends upon the distance of the external field from the magnetic sample). An alternative may be to attach the external permanent magnet or electromagnet to a force and/or torque gauge and measure the force/torque on the external magnet as it approaches the implant.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of any appended claims and any equivalents thereto.

What is claimed is:

1. An implantable strain gauge comprising:
a first plate;
a second plate that is located at a distance from the first plate, the second plate including a window, the second plate being movable relative to the first plate from a first position to a second position upon application of a tension to the strain gauge, the first and second plates being configured to be implanted within tissue;
a luminescent material, the luminescent material emitting a detectable emission upon excitation by irradiation, the emission of the luminescent material being detectable through the tissue, wherein at the first position the emission of the luminescent material is detectable through the window and at the second position either no luminescent emission is detectable through the window or a second luminescent emission is detectable through the window that differs from the emission detected through the window at the first position.

2. The implantable strain gauge of claim 1, wherein the luminescent material is located on an upper surface of the first plate.

3. The implantable strain gauge of claim 2, wherein the luminescent material is located on the upper surface of the first plate in a pattern comprising multiple pattern elements.

4. The implantable strain gauge of claim 1, further comprising a second luminescent material, an emission of the second luminescent material being detectable through the tissue, wherein at the second position, the emission of the second luminescent material is detectable through the transparent window.

5. The implantable strain gauge of claim 1, wherein the second plate includes multiple windows.

6. The implantable strain gauge of claim 1, wherein the emission of the luminescent material is in the visible to near infrared wavelengths.

7. The implantable strain gauge of claim 1, wherein the luminescent material is excited by near-infrared, infrared, or x-ray irradiation.

8. The implantable strain gauge of claim 7, wherein the luminescent material is excited by near-infrared or infrared irradiation and the emission is at near-infrared or infrared wavelengths.

9. The implantable strain gauge of claim 1, wherein the luminescent material is an upconversion material or a surface enhanced Raman spectroscopy material.

10. The implantable strain gauge of claim 1, the strain gauge including a particle that comprises the luminescent material.

11. The implantable strain gauge of claim 1, further comprising an elastomer located between the first plate and the second plate.

12. The implantable strain gauge of claim 11, wherein the luminescent material exhibits a different emission depending upon the pressure of the luminescent material's surrounding environment.

13. The implantable strain gauge of claim 11, further comprising a second luminescent material, at least one of the first and second luminescent materials being a luminescent dye.

14. The implantable strain gauge of claim 1, wherein the first plate is coupled to the second plate.

15. The implantable strain gauge of claim 14, further comprising a wall coupled between the first and second plates.

16. The implantable strain gauge of claim 1, wherein the window is transparent or semi-transparent.

17. The implantable strain gauge of claim 1, wherein the first and second plates are sterilizable.

18. An implantable device comprising the implantable strain gauge of claim 1.

19. The implantable device of claim 18, wherein the implantable device is a fixation device.

20. The implantable device of claim 18, wherein the implantable device comprises an implantable gel.

21. A method for detecting loads on an implant, the method comprising:
    detecting a first emission from a luminescent material through living tissue, the first emission being in response to excitation of the luminescent material by irradiation of the luminescent material, the luminescent material being a component of a strain gauge, the strain gauge being a component of the implant;
    detecting a second emission from the strain gauge through the living tissue; and
    determining a variation in strain placed upon the implant according to the variation between the first emission and the second emission.

22. The method of claim 21, wherein the first emission and the second emission vary by wavelength.

23. The method of claim 21, wherein the first emission and the second emission vary by intensity.

24. The method of claim 21, wherein the first and second emissions are detected through about 10 centimeters or less of tissue.

25. The method of claim 21, wherein the first and second emissions are detected with a camera or a spectrometer.

26. The method of claim 21, further comprising exciting the luminescent material.

27. The method of claim 26, wherein the luminescent material is excited by use of near infrared, infrared, or x-ray irradiation.

* * * * *